United States Patent [19]

Carson

[11] 4,002,643
[45] Jan. 11, 1977

[54] PREPARATION OF β-ACYL PYRROLES

[75] Inventor: John Robert Carson, Norristown, Pa.

[73] Assignee: McNeil Laboratories, Inc., Fort Washington, Pa.

[22] Filed: June 27, 1975

[21] Appl. No.: 590,996

[52] U.S. Cl. .................. 260/326.5 J; 260/45.8 N; 260/326.2; 260/326.47; 260/326.62; 260/326.9; 424/274
[51] Int. Cl.² ........................................ C07D 207/32
[58] Field of Search ............................ 260/326.5 J

[56] References Cited

UNITED STATES PATENTS 3,644,631  2/1972  Pachter et al. .................... 424/274

Primary Examiner—Donald G. Daus
Assistant Examiner—Mary C. Vaughn
Attorney, Agent, or Firm—Geoffrey G. Dellenbaugh

[57] ABSTRACT

A process for rearranging α-acyl pyrroles to β-acyl pyrroles which comprises reacting the former with an excess of a strong, anhydrous, non-oxidizing acid, preferably with heating.

12 Claims, No Drawings

PREPARATION OF β-ACYL PYRROLES

BACKGROUND OF THE INVENTION

The present invention relates to a method of transforming an α-acyl pyrrole (II) having at least one hydrogen atom in the β position into a β-acyl pyrrole (I) as illustrated by the following:

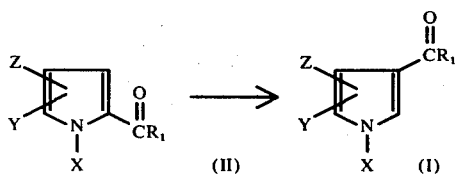

wherein $R_1$ is a member selected from the group consisting of hydrogen, loweralkyl, and aryl. The identity and location of substituents X, Y, and Z are immaterial to the functioning of the method, provided that the substituent on at least one β-position is hydrogen.

More particularly, the present invention relates to a method for preparing from the corresponding α-acyl pyrroles, β-acyl pyrroles having the following formulas:

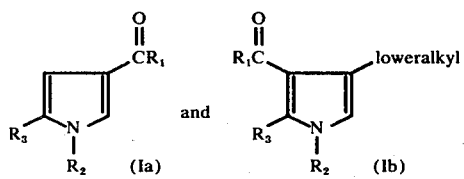

wherein:
$R_1$ is as previously defined;
$R_2$ is a member selected from the group consisting of hydrogen, loweralkyl, aralkyl, and aralkyl substituted with from one to three members each selected from the group consisting of loweralkyl, loweralkoxy, and halo, said aralkyl being a member selected from the group consisting of benzyl and phenethyl; and
$R_3$ is a member selected from the group consisting of hydrogen and loweralkyl.

The above compounds of formula (I) are useful as intermediates for useful ultraviolet light absorbing β-substituted pyrroles of formula:

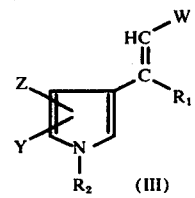

wherein W is $NO_2$ when $R_1$ = H and W is CN when $R_1$ = loweralkyl or aryl. Certain of the compounds of formula (I) wherein $R_1$ is aryl are described in U.S. Pat. No. 3,644,631 as anti-inflammatory, analgesic, and anti-pyretic agents.

The ultraviolet absorbing pyrroles of formula (III) wherein W is $NO_2$ and $R_1$ is H may be prepared by Knoevenagel condensation of the β-pyrrole carboxaldehyde of formula (Ic) with nitromethane as is known in the art. Those wherein W is CN and $R_1$ is loweralkyl or aryl may be prepared by Wadsworth-Emmons condensation of the β-pyrrole ketone of formula (Id) with diethyl cyanomethylphosphonate anion as is known in the art. These two reactions are illustrated below:

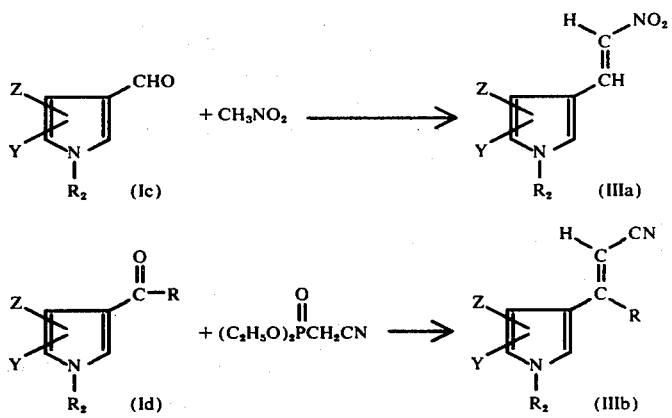

Typical ultraviolet absorption data are shown in Table I below. Because the predominant chromophore is the β-substituted pyrrole olefin, the nature of the other substituents (X,Y,Z) has little or no effect on the absorption.

TABLE I

| Compound | Abs. Max. | ε |
|---|---|---|
| (pyrrole-NH, $NO_2$) | 365 nm | 16,917 |
| (pyrrole-N-$CH_3$, $NO_2$) | 365 nm | 17,818 |

TABLE I-continued

| Compound | Abs. Max. | ε |
|---|---|---|
| (pyrrole structure with CN, CH₃, and N-CH₃ substituents) | 300 nm | 20,500 |

The subject compounds (III) strongly absorb ultraviolet (U.V.) light, generally above 280 nm, and are useful as U.V.-screening materials, for example, in plastic products and sunburn preventive formulations. Because of their general solubility in organic materials, the compounds may be used as U.V.-absorbers in plastics and resins such as, for example, polystyrene, polyethylene, polypropylene, polyacrylics (e.g., methacrylate resins, polyacrylamides, polyacrylonitrile fibers, etc.), polyamide (e.g., nylon) fibers, and polyester fibers. The inclusion of about 0.01–5.0 percent of the absorber, based on the polymer weight, is usually sufficient to render protection against U.V. light, such as in plastic films, light filters, etc. The absorber may be incorporated into the mixture of monomers before polymerization to form the polymer or it may be incorporated into the polymer at other stages during its handling, as by milling into the polymer together with other compounding ingredients, or during the spinning of the polymer into fibers, etc.

DESCRIPTION OF THE INVENTION

The method of the present invention comprises reacting an α-acryl pyrrole of formula (II), where $R_1$ is as previously defined and X, Y, and Z are immaterial, with a strong, anhydrous, non-oxidizing acid such as, for example, polyphosphoric acid, metaphosphoric acid, methanesulfonic acid, trifluoromethanesulfonic acid, toluenesulfonic acid, or the like to cause rearrangement to a corresponding β-acyl pyrrole. A large excess of the acid (generally about ten times the weight by parts of the α-acyl pyrrole), which may also act as the solvent, is preferred. While the rearrangement occurs at ambient temperature for certain α-acyl pyrroles, heating is preferred in the majority of cases to increase the rate of rearrangement and to effect significant rearrangement within a reasonable period of time (e.g., less than 24 hours). The α-acyl pyrrole and the acid are preferably heated together at at least 90° C. and preferably about 90°–120° C. for at least about ½ to about 4 hours. The desired product may be isolated by conventional extraction techniques, for example, by extracting an aqueous basic solution of the reaction mixture with an appropriate inert organic solvent (e.g., an ether such as diethyl ether, an aromatic hydrocarbon such as benzene, toluene, xylene, and the like, a chlorinated hydrocarbon such as methylene chloride, chloroform, and the like, etc.). The product is then conveniently isolated by conventional distillation of the organic extract, preferably at reduced pressure, and purified by standard recrystallization procedures.

More particularly, the method of the invention may be utilized with α-acyl pyrroles of formulas (IIa) and (IIb) to product β-acyl pyrroles of formula (Ia) and (Ib), respectively. This reaction may be illustrated by the following, for compounds of formula (Ia):

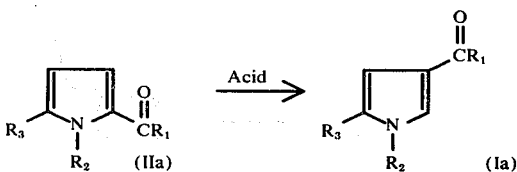

and for compounds of formula (Ib):

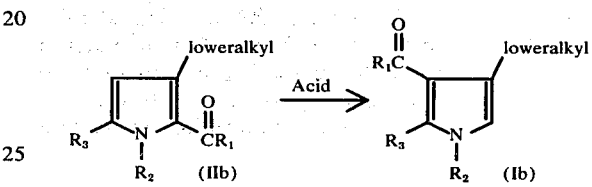

The pyrroles of formulas (IIa) and (IIb) may be prepared by reacting a pyrrole of formula (IV) with an amide of formula (V), where $R_1$, $R_2$, and $R_3$ are as previously defined and where $R_4$ is a member selected from the group consisting of hydrogen and loweralkyl, in the presence of phosphorus oxychloride. Stoichiometric amounts of all reagents are preferred. The reaction is conducted in a suitable inert organic solvent such as, for example, a halogenated hydrocarbon (e.g., 1,2-dichloroethane, carbon tetrachloride, dichloromethane, and the like), an aromatic hydrocarbon (e.g., benzene, toluene, xylene, and the like), or the like. Reflux temperature is preferred. The reaction may be illustrated by the following:

$$\underset{R_2}{\underset{|}{\underset{N}{R_3}}}\overset{R_4}{\diagup} + (CH_3)_2N-\overset{O}{\overset{\|}{C}}R_1 \xrightarrow{POCl_3} \underset{R_2}{\underset{|}{\underset{N}{R_3}}}\overset{R_4}{\diagdown}\overset{O}{\underset{\|}{C}}R_1$$

(IV)     (V)                          (IIa); (IIb)

The amides of formula (V) are generally known or may be prepared by techniques known in the chemical art. The pyrroles of formula (IV) are also generally known in the art.

The pyrroles of formula (IIa) and (IIb) where $R_3$ is loweralkyl, preferably methyl, may also be prepared by decarboxylation of a pyrrole α-loweralkanoic acid of formula (VI), where $R_1$, $R_2$, and $R_4$ are as previously defined and where $R_5$ is a member selected from the group consisting of hydrogen and loweralkyl. The decarboxylation is accomplished by techniques known in the art, as for example, by heating the compound (VI) with or without the presence of a catalyst such as copper chromite, or the like, in a mildly acidic medium such as, for example, propionic acid, toluene plus a catalytic amount of toluene sulfonic acid, and the like, at elevated temperatures such as the reflux temperature of the medium. The desired compound (IIa) or (IIb) may be isolated by extraction techniques well-known in the art. The reaction may be illustrated by the following:

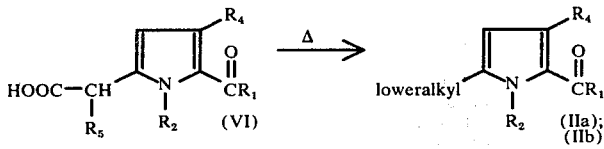

The pyrrole α-loweralkanoic acids of formula (VI) are generally known in the art.

As used herein, the terms "loweralkyl" and "loweralkoxy" mean straight or branch chained, saturated, aliphatic hydrocarbons having from one to about five carbon atoms such as, for example, methyl, ethyl, propyl, isopropyl, butyl, pentyl, and the like loweralkyls and the corresponding loweralkoxy radicals such as, for example, methoxy, ethoxy, propoxy, isopropoxy, butoxy, pentoxy, and the like loweralkoxies. The term "halo" is generic to fluoro, chloro, bromo, and iodo. The term "aryl" includes phenyl, trifluoromethylphenyl, nitrophenyl, and phenyl substituted with from one to three members each selected from the group consisting of loweralkyl, loweralkoxy, and halo.

The following examples are provided to illustrate the process of the invention without intending to limit the scope thereof.

EXAMPLE I

2-p-Chlorobenzoylpyrrole

A mixture of 183 g (1 mole) of p-chloro-N,N-dimethylbenzamide and 153g (1 mole) of phophorous oxychloride in 300 ml of 1,2-dichloroethane is heated under reflux for 30 minutes, after which a solution of 67g (1 mole) of pyrrole in 300 ml of dichloroethane is added drop-wise. It is cooled and a solution of 408g (3 moles) of sodium acetate trihydrate in 1600 ml of water is added dropwise for 45 minutes, after which the mixture is again heated under reflux for 30 minutes. The resulting mixture is poured onto ice, the organic layer is separated, and the aqueous layer is washed with chloroform. The combined organic solutions are washed with sodium bicarbonate and brine and dried over magnesium sulfate. Evaporation of the solvent in vacuo gives a dark oil, which is distilled in vacuo through a heated Vigreaux column to give a white solid; mp 106°–9° C. It is recrystallized from cyclohexane to give 2-p-chlorobenzoylpyrrole as white needles; m.p. 110°–113° C.

EXAMPLE II

The procedure of Example I is repeated substituting an equivalent quantity of the appropriate N,N-dimethylcarboxamide for p-chloro-N,N-dimethylbenzamide and substituting an equivalent quantity of the appropriately substituted pyrrole for pyrrole itself, in order to yield the following respective products:
2-benzoyl-1-methylpyrrole;
2-p-chlorobenzoyl-1-methylpyrrole;
2-p-methylbenzoyl-1-methylpyrrole;
2-m-trifluoromethylbenzoyl-1-methylpyrrole;
2-butyryl-1-methylpyrrole;
2-p-chlorobenzoyl-1-benzylpyrrole;
1-methyl-2-(2,3,6-trimethylbenzoyl)pyrrole;
2-(2,4-dichlorobenzoyl)-1-methylpyrrole;
1-(p-chlorobenzyl)-2-(p-toluoyl)pyrrole;
2-(p-chlorobenzoyl)-1-(n-propyl)pyrrole.

EXAMPLE III

2-p-chlorobenzoyl-1,3,5-trimethylpyrrole

A 15g sample of 5-p-chlorobenzoyl-1,4-dimethylpyrrole-2-acetic acid is heated at 225° C for 2½ hours. The residue is cooled and partitioned between diethyl ether and sodium bicarbonate solution. The ether solution is washed with brine, dried over magnesium sulfate, and evaporated in vacuo. It is recrystallized successively from methanol, hexane, methanol and methylcyclohexane to give 2-p-chlorobenzoyl-1,3,5-trimethylpyrrole as a white solid; m.p. 94°–98° C.

EXAMPLE IV

1,5-Dimethyl-4-(p-toluoyl)pyrrole

A solution of 31.5g (0.1 mole) of sodium 1-methyl-5-p-toluoylpyrrole-2-acetate dihydrate in 300 ml of propionic acid is heated under reflux for 18 hours. The mixture is then poured into water and the precipitated solid is collected by filtration. The solid is dissoled in ether and the resulting solution is washed with sodium bicarbonate solution and brine and dried over magnesium sulfate. After the solvent is evaporated in vacuo, the residue is recrystallized from hexane to give 1,5-dimethyl-4-(p-toluoyl)-pyrrole as a white solid; m.p. 80°–82° C.

EXAMPLE V

3-Benzoyl-1-methylpyrrole

A 48g sample of crude 2-benzoyl-1-methylpyrrole prepared in Example II is added to 500g of polyphosphoric acid and the mixture is stirred at 95° C for 2 hours. It is then poured into ice-water and stirred. The resulting mixture is extracted with diethyl ether and the organic layer is washed with sodium bicarbonate solution and brine and dried over magnesium sulfate. The solvent is evaporated in vacuo and the residue is distilled under reduced pressure through a short Vigreaux column, the product being collected at 134°–145° (0.2 mm). Recrystallization from methanol yields 3-benzoyl-1-methylpyrrole as white solid; m.p. 90°–93° C.

EXAMPLE VI

Following the procedure of Example VII, but substituting the appropriate 2-acylpyrrole of column P where A is COR₁ and B is hydrogen for the 2-benzoyl-1-methylpyrrole used therein, the product 3-acyl pyrroles of column P where A is hydrogen and B is COR₁ are obtained.

The products may be isolated and purified by conventional distillation or recrystallization techniques. Reaction times and temperatures are given, as well as the melting or boiling point of the product.

| P | R₁ | Time (hr) | Temp(° C) | m.p.,(bp) |
|---|---|---|---|---|
| 1-methylpyrrole (N-CH₃, positions A=2, B=3) | p-tolyl | 4 | 95 | (153–7° at .4 mm) |
| " | p-chlorophenyl | 1 | 95 | 48–50 |
| " | m-trifluoromethyl-phenyl | 2½ | 95 | (136–42° at .75 mm) |
| " | methyl | ½ | 95 | (78–81° |
| " | n-propyl | ½ | 95 | at .1 mm) |
| 1-benzylpyrrole (N-CH₂—C₆H₅) | p-chlorophenyl | 3 | 95 | 100–103 |
| 1,2,5-trimethylpyrrole (CH₃, N-CH₃, CH₃) | p-chlorophenyl | 4 | 120 | 103–104 |
| 1,2-dimethylpyrrole (CH₃, N-CH₃) | p-toluoyl | 1 | 95 | 119–120 |
| 2-acetyl-1-methylpyrrole (CH₃C(O), N-CH₃) | p-chlorophenyl | 2¾ | 95 | 102–103 |
| 1-methylpyrrole | 2,4,6-trimethylphenyl | | | |
| " | 2,4-dichlorophenyl | | | |
| 1-(p-chlorobenzyl)pyrrole (N-CH₂C₆H₄Cl) | p-tolyl | | | |
| 1-propylpyrrole (N-CH₂CH₂CH₃) | p-chlorophenyl | | | |

EXAMPLE VII

3-p-Chlorobenzoylpyrrole

A 40g sample of 2-p-chlorobenzoylpyrrole is added to 400g of polyphosphoric acid and the mixture is heated at 95° C for 4 hours under nitrogen. It is then poured into ice water with stirring and the whole is extracted with chloroform. The resulting chloroform solution is washed with sodium bicarbonate solution and brine. It is dried over magnesium sulfate and evaporated to dryness in vacuo. The residue is chromatographed on silica gel, eluting with a step-wise gradient from pure benzene to pure chloroform. The fractions containing product are eluted starting with about 75% chloroform to pure chloroform and are identified by an ultraviolet band at 254 nm. They are combined, concentrated to dryness, and recrystallized successively with benzene and methyl ethyl ketone to give 3-p-chlorobenzoylpyrrole as a tan solid; m.p. 118°–20° C.

EXAMPLE VIII

3-Acetyl-1-Methylpyrrole

A solution of 3.0g of 2-acetyl-1-methylpyrrole in 30 ml of trifluoroacetic acid is heated under reflux for 90 minutes. The solvent is then evaporated in vacuo and the residue is partitioned between chloroform and sodium bicarbonate solution. The chloroform layer is dried and the solvent evaporated in vacuo to give 3-acetyl-1-methylpyrrole as a brown oil.

EXAMPLE IX

1,2-Dimethyl-4-p-toluoylpyrrole

A 1.0g sample of 1,2-dimethyl-5-p-toluoylpyrrole in 10g of dried p-toluenesulfonic acid heated at 105° C for

EXAMPLE X

Methylpyrrole-3-yl Ketone

A solution of 25g of methylpyrrole-2-yl ketone in 250 ml of trifluoroacetic acid is refluxed for ten hours. The solvent is then evaporated in vacuo and the residue is partitioned between chloroform and dilute sodium hydroxide solution. The organic solution is dried over magnesium sulfate, and the solvent is evaporated in vacuo. The residue is chromatographed on Silic AR cc-4. Elution on ether gives first a fraction containing the starting ketone, then a fraction containing the product ketone. The latter is recrystallized from ethyl acetate-hexane and then from benzene-hexane to give methylpyrrole-3-yl ketone; m.p. 113°–115° C. m.p.

EXAMPLE XI

Pyrrole-3-carboxaldehyde

A solution of 10 g. of pyrrole-2-carboxaldehyde in 100 ml. of trifluoromethanesulfonic acid and 100 ml. of 1,2-dichloroethane is heated under reflux for 18 hrs. It is then cooled and poured into an aqueous solution of 350 g. of sodium acetate. The aqueous layer is washed with a mixture of 1,2-dichloroethane and isopropanol and the organic solution is then washed with sodium bicarbonate solution. The sodium bicarbonate wash is combined with the aqueous sodium acetate solution and the whole is allowed to stand for 24 hours after which it is continuously extracted with ether overnight. The ether solution is evaporated in vacuo and the resulting residue is chromatographed on silica gel (Mallinkrodt SilicAR CC-4) with ether. The first compound-bearing fraction contains starting pyrrole-2-carboxaldehyde. The second compound-bearing fraction, upon evaporation of the solvent, yields pyrrole-3-carboxaldehyde. Recrystallization from hexane-carbon tetrachloride yields as brownish crystals, pyrrole-3-carboxaldehyde; m.p. 63°–65° C.

EXAMPLE XII

1-Methylpyrrole-3-carboxaldehyde

A 25g sample of 1-methylpyrrole-2-carboxaldehyde is heated under reflux in 250 ml of trifluoroacetic acid for 6 hours. The trifluoroacetic acid is then evaporated in vacuo and the residue is taken up in chloroform. The chloroform solution is washed with sodium bicarbonate solution, filtered through celite, and dried over magnesium sulfate. The solvent is evaporated in vacuo and the residue is distilled at reduced pressure through a Vigreaux column. The fraction boiling between 78° C at 22 mm and 65° C at 3 mm is composed of starting 1-methylpyrrole-2-carboxaldehyde. The fraction boiling between 70° C at 0.7 mm and 73° C at 0.25 mm is composed mainly of product 1-methylpyrrole-3-carboxaldehyde and is redistilled. The product 1-methylpyrrole-3-carboxaldehyde is distilled at 78°–80° C at 0.5 mm.

1 hour. The solution is then poured into sodium bicarbonate solution and extracted into chloroform. The chloroform is evaporated in vacuo and the residue is recrystallized from ethyl acetate to give 1,2-dimethyl-4-p-toluoylpyrrole as a tan solid; m.p. 117°–119° C.

EXAMPLE XIII

3-p-Chlorobenzoyl-1-methylpyrrole

A solution of 1g of 2-p-chlorobenzoyl-1-methylpyrrole in 10 ml of trifluoromethanesulfonic acid is allowed to stand at ambient temperature for seven days. The solution is then poured into water and the organic materials are extracted with diethyl ether. Evaporation of the solvent from the extract yields a mixture of product and starting material which are separated by column chromatography on silical gel. Successive elution with hexane, hexane-benzene, benzene, benzene-ether yields 2-p-chlorobenzyl-1-methylpyrrole in the first compound-bearing fraction and 3-p-chlorobenzoyl-1-methylpyrrole in the second. Recrystallization of the crude product from pentane yields pure 3-p-chlorobenzoyl-1-methylpyrrole; m.p. 48°–50° C.

EXAMPLE XIV

3-(2-Nitrovinyl)pyrrole

A solution of 2.26g (0.0238 mole) of pyrrole-3-carboxaldehyde, 1.28 ml (0.0238 mole) of nitromethane, 0.405 ml of benzyl amine (0.0038 mole) and 0.21 ml (0.0038 mole) of acetic acid in 8 ml of absolute ethanol is stirred overnight, collected and washed with ethanol to give as a yellow solid 3-(2-nitrovinyl)pyrrole; m.p. 160°–164° C (dec.).

EXAMPLE XV

1-Methyl-3-(2-nitrovinyl)pyrrole

A solution of 14.9g (0.137 mole) of 1-methylpyrrole-3-carboxaldehyde, 7.3 ml (0.137 mole) of nitromethane, 2.3 ml (.021 mole) of benzyl amine and 1.2 ml (.021 mole) of acetic acid in 20 ml of absolute ethanol is warmed briefly and stirred for 6 hours. It is then cooled and the precipitated solid is collected, giving as a yellow solid, 1-methyl-3-(2-nitrovinyl)pyrrole; m.p. 90°–92° C.

EXAMPLE XVI

2-Methyl-2-(1-methylpyrrol-3-yl)-acrylonitrile

Diethyl cyanomethyl-phosphonate (8.1g, 0.045 mole) is added to a suspension of sodium hydride (2.2g 50% NaH washed free of oil, 0.045 mole) in 1,2-dimethoxyethane under nitrogen with cooling. After 1 hour 3-acetyl-1-methyl-pyrrole (6.5g, .053 mole) is added dropwise. The reaction mixture is heated under reflux for 3 hours and is then poured into ice-dilute hydrochloric acid. The resulting white precipitate is collected by filtration and is recrystallized from cyclohexane to give as a white crystallene solid, 2-methyl-2-(1-methylpyrrol-3-yl) acrylonitrile; m.p. 90°–92° C.

Anal. calc'd for $C_9H_{10}N_2$: C 73.94; H, 6.90. Found: C, 74.00; H 6.93.

EXAMPLE XVII

Following the procedure of Example XVIII, but substituting the appropriate β-pyrrole for the 3-acetyl-1-methylpyrrole used therein, there are obtained the following:

2-(n-propyl)-2-(1-methylpyrrol-3-yl acrylonitrile;
2-phenyl-2-(1-methylpyrrol-3-yl) acrylonitrile; and
2-(p-chlorophenyl)-2-(1-methylpyrrol-3-yl) acrylonitrile.

What is claimed is:

1. A process for transforming an α-acyl pyrrole having at least one hydrogen atom in the β- position into a β-acyl pyrrole which comprises reacting said α-acyl pyrrole with a strong, anhydrous, non-oxidizing acid, said "acyl" being a member selected from the group consisting of

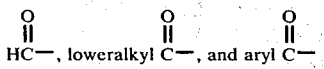

and said "aryl" being a member selected from the group consisting of phenyl, trifluoromethylphenyl, nitrophenyl and phenyl substituted with from one to three members each selected from the group consisting of loweralkyl, loweralkoxy, and halo, said lower alkyl and lower alkoxy groups having 1 to 5 carbon atoms.

2. A process as in claim 1 wherein the strong, anhydrous, non-oxidizing acid is a member selected from the group consisting of polyphosphoric acid, metaphosphoric acid, methanesulfonic acid, trifluoromethanesulfonic acid, toluenesulfonic acid, and trifluoroacetic acid.

3. A process for preparing β-acylpyrroles having a formula selected from the group consisting of:

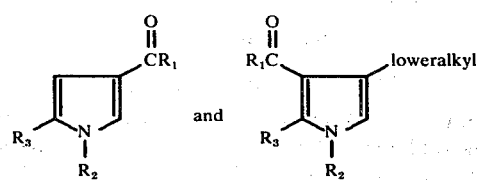

wherein:
$R_1$ is a member selected from the group consisting of hydrogen, loweralkyl, phenyl, trifluoromethyl phenyl, nitrophenyl, and phenyl substituted with from one to three members selected from the group consisting of loweralkyl, loweralkoxy, and halo; $R_2$ is a member selected from the group consisting of hydrogen, loweralkyl, aralkyl and aralkyl substituted on the aryl portion with from one to three members each selected from the group consisting of loweralkyl, loweralkoxy, and halo, said aralkyl being a member selected from the group consisting of benzyl and phenethyl; and $R_3$ is a member selected from the group consisting of hydrogen and loweralkyl;

which comprises reacting with a strong, anhydrous non-oxidizing acid an α-acylpyrrole having a formula selected from the group consisting of:

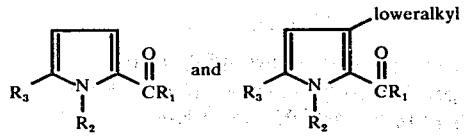

respectively, wherein $R_1$, $R_2$ and $R_3$ are as herein defined.

4. A process for preparing β-acyl pyrroles of formula:

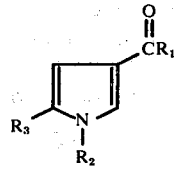

wherein:
$R_1$ is a member selected from the group consisting of hydrogen, loweralkyl, phenyl, trifluoromethyl phenyl, nitrophenyl, and phenyl substituted with from one to three members selected from the group consisting of loweralkyl, loweralkoxy, and halo; $R_2$ is a member selected from the group consisting of hydrogen, loweralkyl, aralkyl, and aralkyl substituted on the aryl portion with from one to three members each selected from the group consisting of loweralkyl, loweralkoxy, and halo, said aralkyl being a member selected from the group consisting of benzyl and phenethyl;

$R_3$ is a member selected from the group consisting of hydrogen and loweralkyl which comprises reacting with a strong, anhydrous, nonoxidizing acid an α-acylpyrrole of formula:

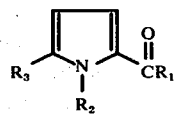

wherein $R_1$, $R_2$, and $R_3$ are as herein defined.

5. A process of preparing β-acylpyrroles of formula:

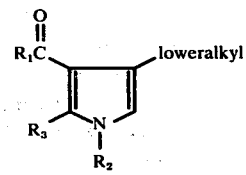

wherein:
$R_1$ is a member selected from the group consisting of hydrogen, loweralkyl, phenyl, trifluoromethyl, phenyl, nitrophenyl, and phenyl substituted with from one to three members selected from the group consisting of loweralkyl, loweralkoxy, and halo; $R_2$ is a member selected from the group consisting of hydrogen, loweralkyl, aralkyl, and aralkyl substituted with from one to three members each selected from the group consisting of loweralkyl, loweralkoxy, and halo, said aralkyl being a member selected from the group consisting of benzyl and phenethyl;

$R_3$ is a member selected from the group consisting of hydrogen and loweralkyl;

which comprises reacting with a strong, anhydrous, nonoxidizing acid, an α-acylpyrrole of formula:

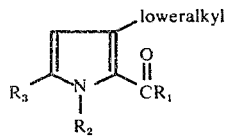

wherein $R_1$, $R_2$ and $R_3$ are as herein defined.

6. A process as in claim 3 wherein the strong, anhydrous, non-oxidizing acid is a member selected from the group consisting of polyphosphoric acid, metaphosphoric acid, methanesulfonic acid, trifluoromethanesulfonic acid, toluenesulfonic acid, and trifluoroacetic acid.

7. A process as in claim 4 wherein the strong, anhydrous, non-oxidizing acid is a member selected from the group consisting of polyphosphoric acid, metaphosphonic acid, methanesulfonic acid, trifluoromethanesulfonic acid, toluenesulfonic acid, and trifluoroacetic acid.

8. A process as in claim 5 wherein the strong, anhydrous, non-oxidizing acid is a member selected from the group consisting of polyphosphoric acid, metaphosphonic acid, methanesulfonic acid, trifluoromethanesulfonic acid, toluenesulfonic acid, and trifluoroacetic acid.

9. A process as in claim 4 wherein there is a large excess of the strong, anhydrous, non-oxidizing acid.

10. A process as in claim 5 wherein there is a large excess of the strong, anhydrous, non-oxidizing acid.

11. A process as in claim 4 which further comprises heating said α-acylpyrrole with said strong, anhydrous, non-oxidizing acid.

12. A process as in claim 5 which further comprises heating said α-acylpyrrole with said strong, anhydrous, non-oxidizing acid.

* * * * *